United States Patent [19]
Kukolja et al.

[11] 4,115,643
[45] Sep. 19, 1978

[54] PROCESS FOR 3-CHLORO CEPHALOSPORINS

[75] Inventors: Stjepan Kukolja, Carmel; Douglas O. Spry, Indianapolis, both of Ind.

[73] Assignee: Eli Lilly and Company, Indianapolis, Ind.

[21] Appl. No.: 822,472

[22] Filed: Aug. 8, 1977

Related U.S. Application Data

[63] Continuation-in-part of Ser. No. 714,948, Aug. 16, 1976, abandoned.

[51] Int. Cl.² .......................................... C07D 501/04
[52] U.S. Cl. ..................................... 544/16; 424/246
[58] Field of Search ........................................... 544/16

[56] References Cited

U.S. PATENT DOCUMENTS

| 3,641,014 | 2/1972 | Murphy et al. ................... 260/243 C |
| 3,925,372 | 12/1975 | Chauvette ............................... 544/16 |
| 3,962,227 | 6/1976 | Chauvette ............................... 544/16 |

*Primary Examiner*—Nicholas S. Rizzo
*Attorney, Agent, or Firm*—William B. Scanlon; Arthur R. Whale

[57] ABSTRACT

7-Acylamido-3-hydroxy-3-cephem-4-carboxylic acid ester sulfoxides are chlorinated and reduced in a single step process with phosphorus trichloride in dimethylformamide to provide 7-acylamido-3-chloro-3-cephem-4-carboxylic acid ester sulfides.

9 Claims, No Drawings

PROCESS FOR 3-CHLORO CEPHALOSPORINS

CROSS REFERENCE TO RELATED APPLICATION

This applicatin is a continuation-in-part of application Ser. No. 714,948 filed Aug. 16, 1976, now abandoned.

BACKGROUND OF THE INVENTION

Cephalosporin antibiotics having a chloro group bonded directly to the 3-position carbon atom of the 3-cephem ring have been described by R. R. Chauvette in U.S. Pat. Nos. 3,925,372 and 3,962,227 and copending application Ser. No. 656,240 filed Feb. 9, 1976, now U.S. Pat. No. 4,064,343. The 3-chloro-3-cephem antibiotics are prepared by the chlorination of a 3-hydroxy-3-cephem ester intermediate, preferably with phosphorus trichloride in the presence of dimethylformamide. The described reaction is illustrated by the following reaction scheme:

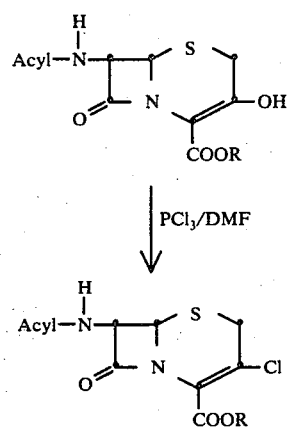

wherein R is a carboxylic acid protecting ester forming group.

The 3-chloro substituted cephalosporins are highly effective in the treatment and control of bacterial infections. In particular, 7-(D-phenylglycylamido)-3-chloro-3-cephem-4-carboxylic acid (U.S. Pat. No. 3,925,372) is highly effective when administered orally. Because of the importance of cephalosporin antibiotics in the treatment of infectious diseases, methods for their economical large scale production are highly desirable.

This invention is concerned with the preparation of 3-chloro substituted cephalosporin antibiotics. In particular, it is concerned with a process for converting 7$\beta$-acylamido-3-hydroxy-3-cephem ester sulfoxides (1-oxides) to the corresponding 7$\beta$-acylamido-3-chloro-3-cephem ester sulfides.

DETAILED DESCRIPTION

The process provided by this invention comprises a one step conversion of a 7$\beta$-acylamido-3-hydroxy-3-cephem ester sulfoxide to a 7$\beta$-acylamido-3-chloro-3-cephem ester sulfide wherein the sulfoxide function is reduced to the normal sulfide state of the cephalosporins and the $C_3$-hydroxy group is converted to the $C_3$-chloro group.

According to the process, a 3-hydroxy-3-cephem sulfoxide ester represented by the formula

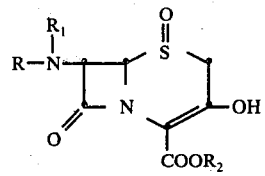

is reacted under substantially anhydrous conditions in the presence of dimethylformamide at a temperature between about 31 65° C. and 25° C. with between about 2 moles and about 9 moles of a chlorinating agent selected from phosphorus trichloride, phosphorus pentachloride and phosgene, per mole of 3-hydroxy-3-cephem sulfoxide ester to provide a 3-chloro-3-cephem ester of the formula

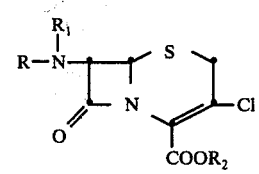

In the above formula, R is an acyl group of the formula

wherein R' is $C_1$-$C_6$ alkyl, phenyl, or phenyl substituted by halogen, $C_1$-$C_4$ alkyl, $C_1$-$C_4$ alkoxy, nitro, or carboxy; or R is an acyl group of the formula

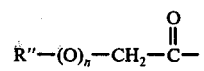

wherein R'' is thienyl, furyl, phenyl, or phenyl substituted by halogen, $C_1$-$C_4$ alkyl, $C_1$-$C_4$ alkoxy, nitro, or carboxy, and n is 0 or 1; such that when n is 1 R'' is other than thienyl or furyl; $R_1$ is hydrogen or $R_1$ and R taken together with the nitrogen atom to which they are attached are succinimido or phthalimido; and $R_2$ is benzyl, 4-methoxybenzyl, 3,5-dimethoxybenzyl, 3,5-diemethoxy-4-hydroxybenzyl, 4-nitrobenzyl, diphenylmethyl, 4-methoxydiphenylmethyl, 2,2,2-trichloroethyl, t-butyl, phenacyl, 4-nitrophenacyl, or methoxymethyl.

In the above definition of R' the term "$C_1$-$C_6$ alkyl" refers to the straight and branched chain saturated alkyl groups such as methyl, ethyl, n-propyl, iso-propyl, n-butyl, sec-butyl, n-pentyl, n-hexyl, and like $C_1$-$C_6$ hydrocarbon groups. The substituted phenyl groups represented by R' and R'' are exemplified by 4-chlorophenyl, 3,4-dichlorophenyl, 2,4-dichlorophenyl, 4-bromophenyl, 2-fluorophenyl, 4-methylphenyl, 3-methylphenyl, 3,4-dimethylphenyl, 4-ethylphenyl, 4-isopropylphenyl, 4-t-butylphenyl, 3-chloro-4-methyl-phenyl, 3,5-dichloro-4-methyl-phenyl, 4-methoxy-3-methylphenyl, 4-methoxyphenyl, 3,4-dimethoxyphenyl, 2-methoxyphenyl, 3-chloro-4-methoxyphenyl, 4-isopropoxyphenyl, 4-t-butyloxyphenyl, 3-bromo-4-methylphenyl, 4-nitrophenyl, 2-nitrophenyl, 3-carboxyphenyl, 2-carboxyphenyl, 3-methyl-4-carboxyphenyl, and like optionally substituted halo, alkyl, alkoxy, nitro, or carboxy phenyl groups.

Representative examples of acyl groups R are acetyl, propionyl, butyryl, benzoyl, 2,6-dimethoxybenzoyl, 4-nitrobenzoyl, 4-methoxybenzoyl, phenylacetyl, 4-chlorophenylacetyl, 3,4-dimethylphenylacetyl, 4-methoxy-3-chlorophenylacetyl, phenoxyacetyl, 4-methoxyphenoxyacetyl, 4-bromophenoxyacetyl, 3,4-dichlorophenoxyacetyl, 2-thienylacetyl, and 2-furylacetyl. When R and $R_1$ are taken together with the nitrogen atom to which they are attached, the diacyl groups are phthalimido or succinimido.

In carrying out the process of this invention, a 3-hydroxy-3-cephem ester sulfoxide represented by the above formula is added to a solution of the chlorinating agent, for example, phosphorus trichloride in dimethylformamide (DMF). The solution is cooled to a temperature between about 0° C. and −60° C. and preferably at about −50° to about −55° C. prior to addition of the sulfoxide. The reaction mixture is agitated, for example by stirring or shaking, as the mixture is allowed to warm to about 20°–25° C. The temperature of the reaction mixture increases during the addition of the sulfoxide and after the addition is complete, the reaction mixture is allowed to warm to about room temperature and is then agitated for an additional time of about 1–2 hours. The reaction can also be carried out by adding the chlorinating agent to a cold solution of the sulfoxide in DMF. However, it is preferably to add the sulfoxide to the chlorinating agent-DMF solution as described above.

Reagent grade DMF is preferred and for best results the DMF is dried over molecular sieve.

As mentioned above, the amount of chlorinating agent used is between about 2 moles and about 9 moles per mole of 3-hydroxy-3-cephem sulfoxide ester. Ratios of chlorinating agent to 3-cephem sulfoxide ester lower than 2:1 result in lower yields of products. Higher ratios of the reagent can be used; however, such excessive amounts are unnecessary when the process conditions described herein are employed. The preferred ratio is about 3–4 moles of chlorinating agent per mole of sulfoxide.

The chlorinating agent-DMF solution is best prepared below about −10° C. The formation of the solution is accompanied by a rise in temperature and cooling is provided to maintain the temperature below about 0° C. to about −10° C. Solutions of the chlorinating agent in DMF prepared above this temperature result in lower yields of the 3-chloro-3-cephem ester product.

The preferred chlorinating agent in the process is phosphorus trichloride.

The process described herein proceeds via the chlorination of the 3-hydroxy group and the reduction of the sulfoxide function to the sulfide or unoxidized state as shown below.

The reduction of cephalosporin sulfoxides with phosphorus trichloride has been previously described by Murphy et al. in U.S,. Pat. No. 3,641,014 issued Feb. 8, 1972, and as mentioned above, the chlorination of 3-hydroxy-3-cephem ester sulfides with phosphorus trichloride is described by R. R. Chauvette in U.S. Pat. No. 3,925,372 issued Dec. 9, 1975. The invention described herein provides a process for preparing 3-chloro-3-cephem esters with 3-hydroxy-3-cephem sulfoxide esters which is carried out in a single step. The starting materials for the process, the 3-hydroxy-3-cephem ester sulfoxides (1-oxides) are far more stable compounds than are the 3-hydroxy-3-cephem esters (sulfide form) previously employed in the preparation of the 3-chloro-3-cephem esters. The sulfoxides used herein are stable on storage and in general are more crystalline. In contrast, the 3-hydroxy-3-cephem esters (sulfide state) are less stable and are more difficult to purify and obtain crystalline. In general, they are best used in the chlorination shortly afte preparation in order to minimize decomposition.

The 3-hydroxy-3-cephem ester sulfoxides are prepared with 3-exomethylenecepham ester sulfoxides as described in co-pending application Ser. No. 625,281 filed Oct. 23, 1975, now U.S. Pat. No. 4,031,084.

According to the method, a 3-exomethylenecepham ester sulfoxide is reacted in the appropriate solvent at a temperature between about −90° and 20° C. with at least two molar equivalents of ozone and the intermediate oxidation products formed are decomposed either thermally or with a mild reducing agent to provide a 3-hydroxy-3-cephem ester sulfoxide.

Solvents which can be used are those solvents which themselves are inert to oxidation by ozone under the conditions employed for the ozonolysis. Suitable solvents are the halogenated hydrocarbon solvents such as methylene chloride, ethylene dichloride, 1,1,2-trichloroethane, the nitriles for example acetonitrile, propionitrile, and butyronitrile, and esters such as methyl acetate or ethyl acetate. Mixtures of such solvents can also be used as well as aqueous solvents, for example aqueous acetone.

It is preferred to use a protic co-solvent which serves as a proton source preventing the formation of cyclic peroxides. Suitable co-solvents which serve as proton sources include the alcohols such as methanol, ethanol, isopropanol, the carboxylic acids such as formic acid, acetic acid, and the higher homologs thereof for example propionic acid. Preferred co-solvents are methanol and acetic acid. Generally between about two and three moles of co-solvent per mole of ester sulfoxide are used.

The preferred temperature range is between about −40° and 5° C.

The concentration of the 3-exomethylenecepham ester sulfoxide in the solvent is not critical; however, concentrations of between about 2 and about 20 percent appear to afford the best results.

The ozone is generated in a standard ozone generator, such as one of those commercially available, which produce ozone by the action of an electric discharge on air or oxygen as it flows through the generator. The stream of ozone containing air or oxygen can be passed directly into the reaction vessel.

In general, the ozone stream is allowed to pass through the reaction mixture for a period of time sufficient to allow at least two equivalents of ozone to pass. Somewhat in excess of two equivalents is generally employed to ensure complete reaction. The reaction can be followed by removing aliquots from the reaction vessel from time to time and assaying the aliquot for the presence of starting material by chromatography. Thin layer chromatography is a convenient and quick way for determining the presence of starting material. Pilot runs also can be employed to determine the length of time of gas passage through reaction mixtures containing given amounts of starting material for common settings on the ozone generator. Alternatively, the amount of ozone generated in the air or oxygen stream can be predetermined for given voltage and flow settings on the ozonizer.

The intermediate oxidation products formed in situ during the ozonolysis are decomposed either thermally or by treating the reaction mixture with a mild reducing agent. When the ozonolysis of the 3-exomethylenecepham ester sulfoxide is carried out at temperatures much below 0°, for example at about −30° C., the reaction mixture can be warmed to between about 0° to about 45° C. to effect the decomposition. Alternatively, the ozonide can be thermally decomposed more rapidly by adding a higher boiling solvent to the reaction mixture and then evaporating the solvent from the reaction mixture with heat.

The intermediate oxidation products also can be decomposed by adding to the reaction mixture a mild reducing agent and preferably one which will not interfere with the isolation of the product. Suitable reducing agents include for example dimethyl sulfide, sulfur dioxide, sodium bisulfite and trimethyl phosphite. Dimethyl sulfide and sulfur dioxide are preferred reducing agents. In general, somewhat in excess of one mole of the reducing agent per mole of the starting material is used in the decomposition. The reducing agent is generally added at the temperature at which the ozonolysis has been carried out.

In an example of the method for preparing the starting materials, p-nitrobenzyl 7-phenoxyacetamido-3-exomethylenecepham-4-carboxylate-1-oxide is dissolved in acetonitrile containing about 2.5 percent (v:v) of acetic acid and the solution is cooled to about −15° C. Ozone is passed through the reaction mixture until all starting material has reacted. Dimethyl sulfide is added to the reaction mixture which is then allowed to stir for 30 minutes at the reaction temperature of −15° C. The product, p-nitrobenzyl 7-phenoxyacetamido-3-hydroxy-3-cephem-4-carboxylate-1-oxide which forms as a precipitate is filtered. The filtered product is washed with cold solvent and vacuum dried.

The 3-exomethylenecepham sulfoxide esters can be obtained by the process described by S. Kukolja in copending application Ser. No. 673,036 filed Apr. 2, 1976 now U.S. Pat. No. 4,052,387. According to the described method, a 6-acylamidopenicillanic acid ester sulfoxide is reacted with an excess of N-chlorosuccinimide in a dry, inert organic solvent, such as 1,1,2-trichloroethane or toluene, at a temperature between about 70° and 100° C. to provide an azetidinone sulfinyl chloride. The azetidinone sulfinyl chloride is formally named 3-methyl-2-(2-chlorosulfinyl-4-oxo-3-acylamido-1-azetidinyl)-3-butenoic acid ester.

The azetidinone sulfinyl chloride is then reacted with a Lewis acid Friedel-Crafts type catalyst in a dry, inert organic solvent to effect cyclization and provide the 3-exomethylenecepham sulfoxide ester.

The foregoing reaction sequence is illustrated by the following reaction scheme.

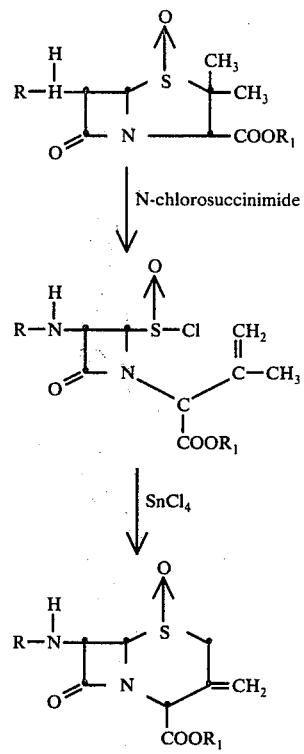

Lewis acid-Friedel Crafts catalysts which are useful in the cyclization of the azetidinone sulfinyl chloride include for example stannic chloride, zinc chloride, zinc bromide, titanium tetrachloride, and zirconium tetrachloride. Stannic chloride is a preferred catalyst in the cyclization. The cyclization is carried out in an inert solvent preferably an aprotic organic solvent, for example aromatic hydrocarbons, such as benzene, toluene, xylene, nitrobenzene, and the like; and halogenated aliphatic hydrocarbons such as methylene chloride, 1,2-dichlorethane and 1,1,2-trichloroethane.

The cyclization can be carried out at a temperature between about 20° and about 85° C.

In an example of the foregoing preparation, a solution of p-nitrobenzyl 6-phenoxyacetamidopenicillanate sulfoxide in dry toluene is treated with 1.1 molar equivalents of N-chlorosuccinimide and the reaction mixture is refluxed for about 90 minutes. The reaction mixture containing p-nitrobenzyl 3-methyl-2-(2-chlorosulfinyl-4-oxo-3-phenoxyacetamido-1-azetidinyl)-3-butenoate, is cooled to a temperature of about 50° C. and 1.1 molar equivalents of anhydrous stannic chloride are added. The mixture thus obtained is stirred at room temperature for about 90 minutes. Water and ethyl acetate are added to the reaction mixture and the organic layer is separated. The organic layer containing the product is washed with dilute acid, dilute sodium bicarbonate solution, and finally with brine. The washed organic layer is then dried and evaporated to yield p-nitrobenzyl 7-phenoxyacetamido-3-exomethylenecepham-4-carboxylate-1-oxide.

Examples of 7β-acylamido-3-hydroxy-3-cephem-4-carboxylic acid sulfoxide esters which are used in the chlorination-reduction process of this invention are the sulfoxides of the following: 4-nitrobenzyl 7-phenylacetamido-3-hydroxy-3-cephem-4-carboxylate, 2,2,2-trichloroethyl 7-phenylacetamido-3-hydroxy-3- cephem-4-carboxylate, 4-methoxybenzyl 7-phenylacetamido-3-hydroxy-3-cephem-4-carboxylate, diphenylmethyl 7-phenylacetamido-3-hydroxy-3-cephem-4-carboxylate, 4-nitrobenzyl 7-phenoxyacetamido-3-hydroxy-3-cephem-4-carboxylate, diphenylmethyl 7-phenoxyacetamido-3-hydroxy-3-cephem-4-carboxylate, 2,2,2-trichloroethyl 7-phenoxyacetamido-3-hydroxy-3-cephem-4-carboxylate, 4-methoxybenzyl 7-phenoxyacetamido-3-hydroxy-3-cephem-4-carboxylate, t-butyl 7-phenoxyacetamido-3-hydroxy-3-cephem-4-carboxylate, 4-nitrobenzyl 7-(2-thienylacetamido)-3-hydroxy-3-cephem-4-carboxylate, diphenylmethyl 7-(2-thienylacetamido)-3-hydroxy-3-cephem-4-carboxylate, benzyl 7-(2-thienylacetamido)-3-hydroxy-3-cephem-4-carboxylate, methoxymethyl 7-(2-thienylacetamido)-3-hydroxy-3-cephem-4-carboxylate, diphenylmethyl 7-(2-furylacetamido)-3-hydroxy-3-cephem-4-carboxylate, benzyl 7-(2-furylacetamido)-3-hydroxy-3-cephem-4-carboxylate, 4-nitrobenzyl 7-acetamido-3-hydroxy-3-cephem-4-carboxylate, diphenylmethyl 7-acetamido-3-hydroxy-3-cephem-4-carboxylate, benzyl 7-acetamido-3-hydroxy-3-cephem-4-carboxylate, 2,2,2-trichloroethyl 7-acetamido-3-hydroxy-3-cephem-4-carboxylate, 4-methoxybenzyl 7-propionamido-3-hydroxy-3-cephem-4-carboxylate, phenacyl 7-(4-chlorophenylacetamido)-3-hydroxy-3-cephem-4-carboxylate, 4-nitrobenzyl 7-phthalimido-3-hydroxy-3-cephem-4-carboxylate, 4-nitrophenacyl 7-phthalimido-3-hydroxy-3-cephem-4-carboxylate, diphenylmethyl 7-succinimido-3-hydroxy-3-cephem-4-carboxylate, diphenylmethyl 7-phthalimido-3-hydroxy-3-cephem-4-carboxylate, benzyl 7-phthalimido-3-hydroxy-3-cephem-4-carboxylate, 4-nitrobenzyl 7-benzamido-3-hydroxy-3-cephem-4-carboxylate, diphenylmethyl 7-(2,6-dimethoxybenzamido)-3-hydroxy-3-cephem-4-carboxylate, and 4-nitrobenzyl 7-(4-methoxyphenylacetamido)-3-hydroxy-3-cephem-4-carboxylate.

Preferred 3-hydroxy-3-cephem sulfoxide esters are represented by the following formula

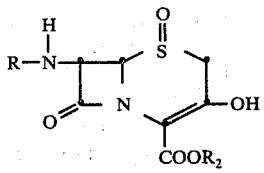

wherein R is phenoxyacetyl, phenylacetyl, or thienylacetyl, and $R_2$ is 2,2,2-trichloroethyl, benzyl, diphenylmethyl, 4-methoxybenzyl, or 4-nitrobenzyl. These 3-hydroxy sulfoxide esters are preferred because of their ready availability from penicillins obtained cheaply via fermentation.

An especially preferred starting material is 4-nitrobenzyl 7-phenoxyacetamido-3-hydroxy-3-cephem-4-carboxylate sulfoxide.

In a preferred embodiment of this invention, phosphorus trichloride is dissolved in DMF cooled to a temperature of −50° C. and dry, pulverized 4-nitrobenzyl 7-phenoxyacetamido-3-hydroxy-3-cephem-4-carboxylate sulfoxide is added to the cold solution with stirring. After addition of the sulfoxide is complete, the temperature of the reaction mixture is increased to about 25° C. and stirring is continued for 1–2 hours.

The reaction mixture is then shaken with methylene chloride, ice, and cold water. The methylene chloride extract is separated and is washed several times with salt water before drying with anhydrous magnesium sulfate. The extract is evaporated to dryness to yield 4-nitrobenzyl 7-phenoxyacetamido-3-chloro-3-cephem-4-carboxylate.

In a further embodiment of the invention, 4-nitrobenzyl 7-phenylacetamido-3-hydroxy-3-cephem-4-carboxylate sulfoxide (0.1 mole) is added to a solution of 3.5 moles of $PCl_3$ in 500 ml. of DMF maintained at a temperature of about −50° C. After stirring for 1 hour in the cold, the temperature is increased to about 20° C. and stirring is continued for 1 hour. Thereafter, the reaction mixture is diluted with ice water and is extracted with cold ethyl acetate. The extract is washed with dilute sodium bicarbonate solution and with salt water and is then dried. The extract is then evaporated to yield 4-nitrobenzyl 7phenylacetamido-3-chloro-3-cephem-4-carboxylate.

In another embodiment of this invention, diphenylmethyl 7-(2-thienylacetamido)-3-hydroxy-3-cephem-4-carboxylate sulfoxide is reacted with $PCl_3$ in DMF at a temperature of about −30° C., the reaction mixture warmed to a temperature of about 25° C. and the product, diphenylmethyl 7-(2-thienylacetamido)-3-chloro-3-cephem-4-carboxylate, is recovered from the mixture by extraction with methylene chloride.

The 3-chloro cephalosporin esters provided by the process of this invention are useful intermediates to 3-chloro cephalosporin acid antibiotics described by Chauvette in U.S. Pat. Nos. 3,925,372 and 3,962,227 and in copending application Ser. No. 656,240 filed Feb. 9, 1976 now U.S. Pat. No. 4,064,343. The ester group of the products is removed according to known de-esterification procedures to provide the free acid antibiotic. For example, the t-butyl ester is removed with 90% formic acid; the benzyl group is removed via hydrogenolysis as is the 4-nitrobenzyl ester group; the 4-nitrobenzyl group is also removed with zinc and acid; the diphenylmethyl ester group is removed with trifluoroacetic acid in anisole as is the 4-methoxybenzyl group. The 2,2,2-trichloroethyl ester group is removed with zinc and acid.

The present process is useful in an overall process for the preparation of the 3-chlorocephalosporin antibiotics from relatively inexpensive penicillins produced via fermentation. For example, penicillin V sodium salt (6-phenoxyacetamidopencillanic acid sodium salt) is esterified with 4-nitrobenzyl bromide and the ester is oxidized with m-chloroperbenzoic acid to 4-nitrobenzyl 6-phenoxyacetamidopenicillanate sulfoxide. The sulfoxide ester is reacted with N-chlorosuccinimide to cleave the penam thiazolidine ring to provide an azetidinone sulfinyl chloride and the latter is cyclized to 4-nitrobenzyl 7-phenoxyacetamido-3-exomethylenecepham-4-carboxylate sulfoxide with a Lewis acid Friedel-Crafts catalyst, as descriged by Kukolja supra. Ozonolysis of the 3-exomethylene ester as described previously herein yields the 3-hydroxy-3-cephem ester, the starting materials of the present process. The chlorination reduction process of this invention is then carried out on the 4-nitrobenzyl 7-phenoxyacetamido-3-hydroxy-3-cephem-4-carboxylate sulfoxide and the product de-esterified with zinc and acid to provide 7-phenoxyacetamiod-3-chloro-3-cephem-4-carboxylic acid.

As previously mentioned, a highly effective 3-halo cephalosporin is 7-(D-phenylglycylamido)-3-chloro-3-cephem-4-carboxylic acid. The products of the present process can also be used as intermediates in the synthesis of this valuable antibiotic. For example, the phenoxyacetyl side chain of 4-nitrobenzyl 7-phenoxyacetamido-3-chloro-3-cephem-4-carboxylate can be removed via N-deacylation to provide the 7-amino-3-chloro-3-cephem ester nucleus compound, 4-nitrobenzyl 7-amino-3-chloro-3-cephem-4-carboxylate. The 7-amino nucleus ester can be acylated with, e.g., D-phenylglycyl chloride hydrochloride, as described by Chauvette in U.S. Pat. No. 3,925,372 to provide after de-esterification the orally effective antibiotic.

The N-deacylation of a product of the process is carried out by the known side chain cleavage reaction. The cleavage reaction comprises formation of an imino chloride of the amido side chain with phosphorus pentachloride, and addition of an alcohol such as methanol or iso-butanol to form an unstable imino ether. Decomposition of the imino ether affords the 7-amino-3-chloro nucleus ester compound.

The process of this invention is further illustrated by the following examples.

EXAMPLE 1

4-Nitrobenzyl 7-phenoxyacetamido-3-chloro-3-cephem-4-carboxylate

To 20 ml. of dimethylformamide cooled to −10° C. were added 1.31 ml. ($d = 1.57$) of phosphorus trichloride with stirring. The solution was allowed to stir 10 minutes and was cooled to about −55° C. by means of a dry ice-acetone bath. To the cold solution was added dropwise a cold solution of 2.51 g. (5 mmoles) of 4-nitrobenzyl 7-phenoxyacetamido-3-hydroxy-3-cephem-4-carboxylate sulfoxide in 40 ml. of DMF. Following addition, the mixture was stirred in an ice-salt bath at −7° C. for 1 hour and at room temperature for 1 hour. The reaction mixture was extracted with ethyl acetate and the extract was washed twice with a dilute solution of sodium bicarbonate, twice with salt water and was then dried. The extract was next evaporated in vacuo. The crude product was purified by chromatography over 10 g. of silica gel by employing the gradient:600 ml. of toluene to 600 ml. of 1:1 ethyl acetate:toluene, v:v. The yield of purified product was 0.967 g. (38.5% yield).

EXAMPLE 2

To a cold (−55° C.) solution of 30 ml. of DMF (reagent grade and dried with molecular sieve) were added 2.05 ml. of reagent grade phosphorus trichloride. To this cold solution were added 4.0 g. (8.0 mmole) of solid 4-nitrobenzyl 7-phenoxyacetamido-3-hydroxy-3-cephem-4-carboxylate sulfoxide with the aid of a 2 ml. DMF. Forty minutes following the addition, the temperature of the reaction mixture had increased to about 25° C. The mixture was stirred for about 90 minutes at 25° C. The product was recovered as follows: 30 ml. of methylene were added to the mixture along with 60 g. of ice and 35 ml. of water. The mixture was shaken and the methylene chloride extract separated. The extract was washed 5 times with 45 ml. portions each of ice water containing 0.6 g. of sodium chloride. The extract was then dried by stirring with 1.5 g. of anhydrous magnesium sulfate.

The dried extract containing the product 4-nitrobenzyl 7-phenoxyacetamido-3-chloro-3-cephem-4-carboxylate was brought up to a volume of 38 ml. with methylene chloride. The solution was cooled to −15° C. and was treated successively with 0.90 ml. of pyridine and 2.08 g. of phosphorus pentachloride. The mixture was stirred for 1 hour at 20°-25° C., was cooled to 0° C. and 4.64 ml. of iso-butanol were added. The mixture was then stirred for 3 hours at room temperature while the N-deacylated product, 4-nitrobenzyl 7-amino-3-chloro-3-cephem-4-carboxylate crystallized. The product was filtered at 10° C. and was washed with methylene chloride. The product was dried to yield 2.03 g. (62.6% yield).

EXAMPLE 3

To a cold (−50° C.) solution of 2.45 ml. of phosphorus trichloride in 30 ml. of DMF is added 3.9 g. (8 mmole) of 2,2,2-trichloroethyl 7-(2-thienylacetamido)-3-hydroxy-3-cephem-4-carboxylate sulfoxide. A small amount (ca. 2-3 ml.) of DMF is used to flush in the sulfoxide ester. The reaction mixture is stirred for 1 hour, the temperature is increased to about 20° C. and stirring continued for 1 hour. The reaction mixture is treated with methylene chloride and ice water and is shaken. The methylene chloride is separated and is washed several times with water and with salt water before drying over anhydrous magnesium sulfate. The dried extract is evaporated to provide 2,2,2-trichloroethyl 7-(2-thienylacetamido)-3-chloro-3-cephem-4-carboxylate.

EXAMPLE 4

A solution of 4.95 g. (10 mmole) of p-nitrobenzyl 7-phthalimido-3-exomethylenecephem-4-carboxylate sulfoxide in 100 ml. of methylene chloride was cooled to a temperature of −70° C. Ozone was then passed through the cold solution until the solution turned blue. The cold solution was treated with sulfur dioxide and evaporated to dryness yielding 4.0 g. of p-nitrobenzyl 7-phthalimido-3-hydroxy-3-cephem-4-carboxylate sulfoxide as a solid residue.

The product was dissolved in dimethylformamide and the solution cooled to ice bath temperature. To the solution were slowly added with stirring 0.93 ml. (10.5 mmole) of phosphorus trichloride and after the addition was complete, the reaction mixture was stirred for 1 hour. A 70 ml. mixture of ice and water was added to the mixture and the product precipitated and was filtered. The product was washed with water and dilute hydrochloric acid and was dried to yield 4.0 g. of p-nitrobenzyl 7-phthalimido-3-chloro-3-cephem-4-carboxylate. Thin layer chromatography showed the product was contaminated with a minor amount of the 3-exomethylenecepham ester sulfoxide.

The product was purified via chromatography over a silica gel packed column (3 × 20 cm.) by eluting with toluene:ethyl acetate (95:5, v:v). The fractions containing the 3-chloro product (TLC) were combined and evaporated to dryness under vacuum to give 2.70 g. The purified product can be recrystallized from methylene chloride-cyclohexane.

A sample of the product, p-nitrobenzyl 7-phthalimido-3-chloro-3-cephem-4-carboxylate prepared and purified as described above gave the following elemental analysis for $C_{22}H_{14}N_3O_7S_1Cl_1$:

Theory: C, 52.86; H, 2.82; N, 8.41; O, 22.40; S, 6.41; Cl, 7.09. Found: C, 52.60; H, 3.03; N, 8.29; O, 22.56; S, 6.14; Cl, 7.26.

EXAMPLE 5

To 20 ml. of dimethylformamide cooled to a temperature between about −30° C. and about −50° C. and maintained in an atmosphere of argon were added with stirring 1.04 ml. of phosgene. An exothermic reaction ensued which was allowed to proceed at 0° C. for about 5 minutes. The solution was degassed with argon and cooled briefly in an acetone-dry ice bath. To the cold solution was added dropwise a solution of 2.51 g. of p-nitrobenzyl 7-phenoxyacetamido-3-hydroxy-3-cephem-4-carboxylate sulfoxide in 40 ml. of dimethylformamide. The reaction mixture was stirred for one hour with cooling in a brine-ice bath (−7° C.) and for 1 hour at room temperature. The product was extracted with ethyl acetate and the extract was washed and dried to yield the crude product; p-nitrobenzyl 7-phenoxyacetamido-3-chloro-3-cephem-4-carboxylate. The product was purified by chromatography yielding 0.627 g. (24.9% yield) of purified material.

We claim:

1. The process for preparing a 3-chloro-3-cephem ester of the formula

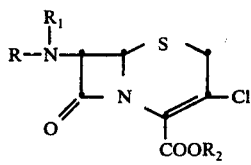

which comprises the step of reacting a 3-hydroxy-3-cephem sulfoxide ester of the formula

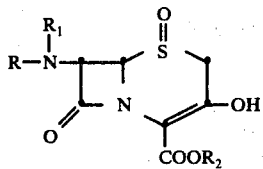

under substantially anhydrous conditions in the presence of dimethylformamide at a temperature between about −65° C. and about 25° C. with between about 2 and about 9 moles of a chlorinating agent selected from the group of phosphorus trichloride, phosphorus pentachloride and phosgene, per mole of said sulfoxide ester wherein R is an acyl group of the formula

wherein R' is $C_1$–$C_6$ alkyl, phenyl, or phenyl substituted by halogen, $C_1$–$C_4$ alkyl, $C_1$–$C_4$ alkoxy, nitro, or carboxy; or R is an acyl group of the formula

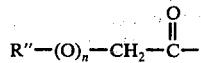

wherein R'' is thienyl, furyl, phenyl, or phenyl substituted by halogen, $C_1$–$C_4$ alkyl, $C_1$–$C_4$ alkoxy, nitro, or carboxy, $n$ is 0 or 1; and when $n$ is 1 R'' is other than thienyl or furyl; $R_1$ is hydrogen or $R_1$ and R taken together with the nitrogen atom to which they are attached are succinimido or phthalimido; and $R_2$ is benzyl, 4-methoxybenzyl, 3,5-dimethoxybenzyl, 3,5-dimethoxy-4-hydroxybenzyl, 4-nitrobenzyl, diphenylmethyl, 4-methoxydiphenylmethyl, 2,2,2-trichloroethyl, t-butyl, phenacyl, 4-nitrophenacyl, or methoxymethyl.

2. The process of claim 1 wherein phosphorus trichloride in the chlorinating agent.

3. The process of claim 2 wherein between about 3 and about 4 moles of phosphorus trichloride per mole of 3-hydroxy-3-cephem sulfoxide ester is used.

4. The process of claim 3 wherein the reaction is carried out at a temperature between about −55° C. and about 0° C.

5. The process of claim 1 wherein R is phenylacetyl, phenoxyacetyl, or thienylacetyl, $R_1$ is hydrogen, and $R_2$ is 2,2,2-trichloroethyl, benzyl, diphenylmethyl, 4-methoxybenzyl, or 4-nitrobenzyl 6. The process of claim 5 wherein R is phenoxyacetyl and $R_2$ is 4-nitrobenzyl.

7. The process of claim 6 wherein between about 3 and about 4 moles of phosphorus trichloride per mole of 3-hydroxy-3-cephem sulfoxide ester is used.

8. The process of claim 1 wherein R and $R_1$ are taken together and represent phthalimido.

9. The process of claim 8 wherein $R_2$ is 4-nitrobenzyl.

* * * * *